(12) United States Patent
Essalik et al.

(10) Patent No.: US 9,986,979 B2
(45) Date of Patent: Jun. 5, 2018

(54) NON-INVASIVE BIOMEDICAL DETECTION AND MONITORING SYSTEMS

(75) Inventors: Abdeltif Essalik, Quebec (CA); André Dussault, Québec (CA); JalalEddine Essalik, Safi (MA)

(73) Assignee: INVAFREE HMS, INC., Chemin du Fleuve, Lévis QC (CA)

( * ) Notice: Subject to any disclaimer, the term of this patent is extended or adjusted under 35 U.S.C. 154(b) by 1375 days.

(21) Appl. No.: 13/202,038

(22) PCT Filed: Feb. 19, 2010

(86) PCT No.: PCT/CA2010/000235
§ 371 (c)(1),
(2), (4) Date: Oct. 31, 2011

(87) PCT Pub. No.: WO2010/094131
PCT Pub. Date: Aug. 26, 2010

(65) Prior Publication Data
US 2012/0041288 A1 Feb. 16, 2012

(30) Foreign Application Priority Data
Feb. 20, 2009 (CA) ..................... 2655017

(51) Int. Cl.
*A61B 5/05* (2006.01)
*A61B 10/00* (2006.01)
(Continued)

(52) U.S. Cl.
CPC ...... *A61B 10/0045* (2013.01); *A61B 5/14514* (2013.01); *A61B 5/14546* (2013.01);
(Continued)

(58) Field of Classification Search
CPC ........... A61B 5/01; A61B 5/1468; A61B 5/15; A61B 5/157; A61B 5/1455;
(Continued)

(56) References Cited

U.S. PATENT DOCUMENTS

| 4,775,361 A | 10/1988 | Jacques et al. |
| 5,423,803 A | 6/1995 | Tankovich |

(Continued)

FOREIGN PATENT DOCUMENTS

| WO | WO 94/09713 | 5/1994 |
| WO | WO 00/78207 | 12/2000 |
| WO | 01/13989 | 3/2001 |
| WO | WO 01/62144 | 8/2001 |

OTHER PUBLICATIONS

DermaWave Systems History, 2007.
(Continued)

*Primary Examiner* — Jacqueline Cheng
*Assistant Examiner* — Eric Messersmith
(74) *Attorney, Agent, or Firm* — Norton Rose Fulbright Canada LLP

(57) ABSTRACT

The present disclosure relates to a non-invasive and continuous biomedical detections and non-invasive and continuous monitoring methods and devices for extracting and analyzing interstitial fluid extracted non-invasively and continuously from the skin of a subject comprising non-invasively electroporating the skin using a non pulsed voltage in combination with a pulsed voltage and applying negative pressure.

44 Claims, 6 Drawing Sheets

(51) Int. Cl.
*A61B 5/145* (2006.01)
*A61B 5/151* (2006.01)
*A61B 5/155* (2006.01)
*A61N 1/04* (2006.01)
*C12Q 1/00* (2006.01)
*A61B 5/15* (2006.01)
*A61B 18/14* (2006.01)
*A61B 18/00* (2006.01)
*A61N 1/32* (2006.01)

(52) U.S. Cl.
CPC ........ *A61B 5/155* (2013.01); *A61B 5/150022* (2013.01); *A61B 5/15087* (2013.01); *A61B 5/150099* (2013.01); *A61B 5/15134* (2013.01); *A61B 5/150221* (2013.01); *A61B 5/150229* (2013.01); *A61B 5/150954* (2013.01); *A61N 1/0412* (2013.01); *C12Q 1/006* (2013.01); *A61B 5/14532* (2013.01); *A61B 18/14* (2013.01); *A61B 2010/008* (2013.01); *A61B 2018/00613* (2013.01); *A61N 1/0424* (2013.01); *A61N 1/327* (2013.01)

(58) Field of Classification Search
CPC ............ A61B 10/0045; A61B 5/14514; A61B 5/14546; A61B 5/150022; A61B 5/150099; A61B 5/150221; A61B 5/150229; A61B 5/15087; A61B 5/150954; A61B 5/15134; A61B 5/155; A61B 5/14532; A61B 18/14; A61N 1/0412; C12Q 1/006
See application file for complete search history.

(56) References Cited

U.S. PATENT DOCUMENTS

| | | | |
|---|---|---|---|
| 5,534,132 A * | 7/1996 | Vreeke | G01N 33/5438 204/403.14 |
| 5,730,714 A | 3/1998 | Guy et al. | |
| 5,983,131 A | 11/1999 | Weaver | |
| 2002/0010414 A1 * | 1/2002 | Coston | A61B 5/14514 604/20 |
| 2002/0038101 A1 | 3/2002 | Avrahami et al. | |
| 2002/0169394 A1 * | 11/2002 | Eppstein | A61B 5/00 600/573 |
| 2002/0177788 A1 * | 11/2002 | Hodges | A61B 5/1411 600/583 |
| 2003/0023189 A1 * | 1/2003 | Kuo | A61B 5/14532 600/584 |
| 2003/0191376 A1 * | 10/2003 | Samuels | A61B 5/00 600/309 |
| 2006/0058602 A1 * | 3/2006 | Kwiatkowski | A61B 5/14514 600/407 |
| 2008/0208107 A1 * | 8/2008 | McRae | A61N 1/0412 604/20 |
| 2008/0262334 A1 * | 10/2008 | Dunn | A61B 5/14532 600/365 |

OTHER PUBLICATIONS

501(k) Summary Statement for the DermaWave 5000 Combi Max System, Mar. 17, 2004.
International Search Report for PCT/CA2010/000235.
Lee et al., 2010, Gut and Liver, 4(suppl. 1): S99-S104.

* cited by examiner

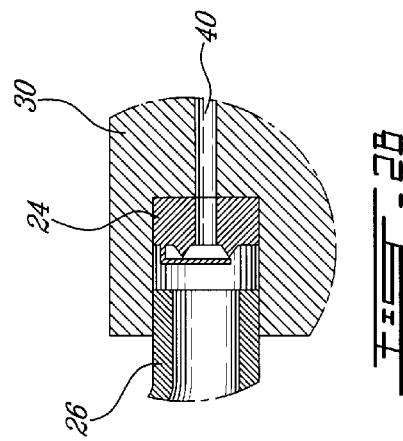
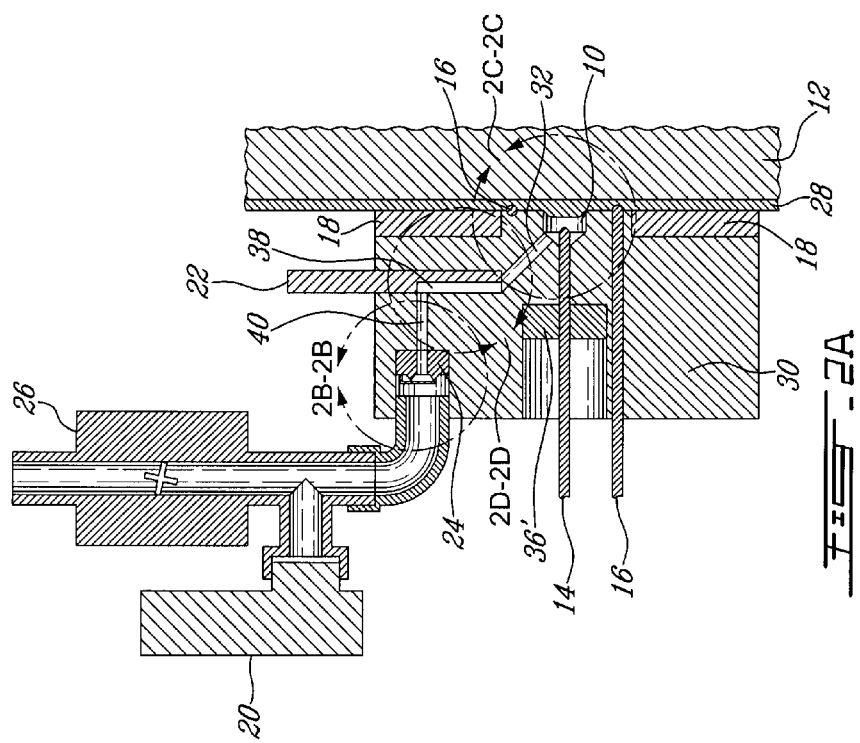

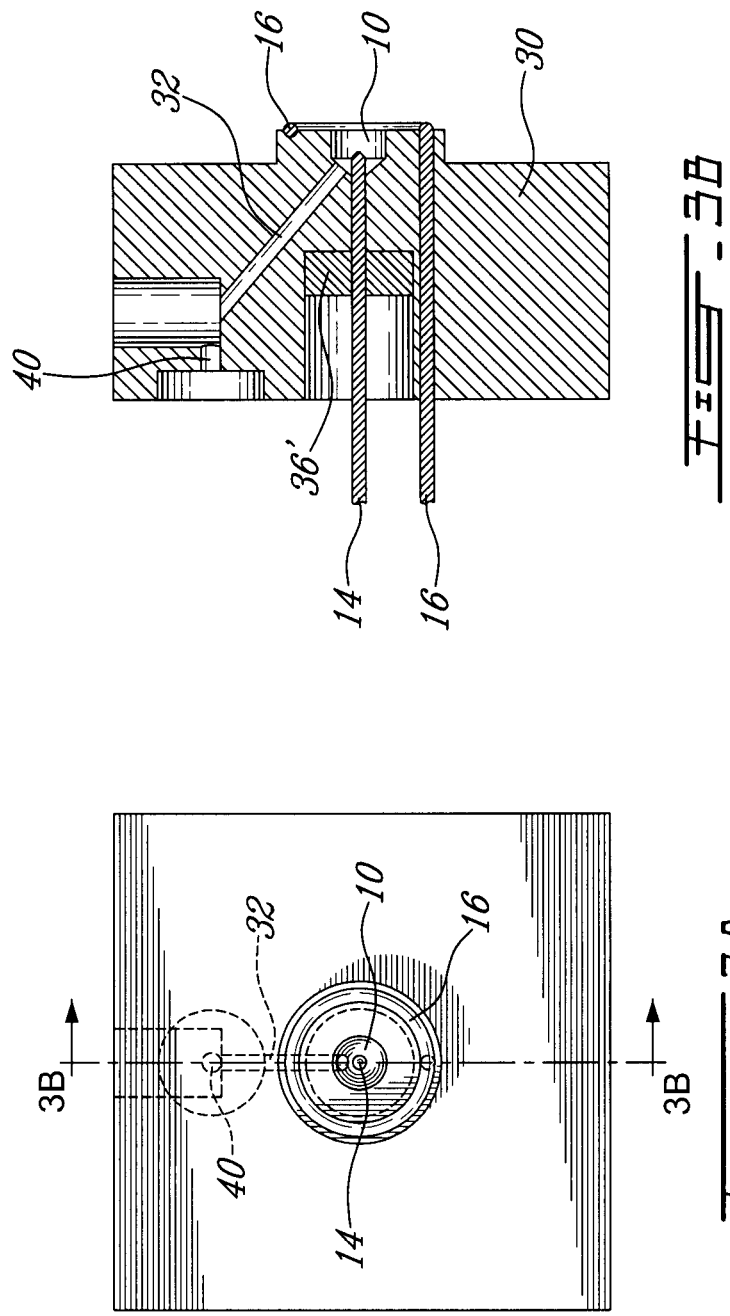

NON-INVASIVE BIOMEDICAL DETECTION AND MONITORING SYSTEMS

CROSS-REFERENCE TO RELATED APPLICATIONS

The present application is the U.S. Nationalization Application of International Patent Application Number PCT/CA2010/000235, which claims priority on Canadian patent application number 2,655,017 filed Feb. 20, 2009, the entire content of which is incorporated herein by reference.

TECHNICAL FIELD

The present disclosure relates to the non-invasive and continuous biomedical detection and/or non-invasive continuous monitoring methods and devices by irreversibly electroporating the skin of a subject so as to non-invasively and continuously extract the interstitial fluid trough the skin.

BACKGROUND ART

Early disease detection and disease monitoring are critical factors in diagnosing the correct physical symptoms and establishing the appropriate therapies. Plasma is frequently used as a material for the diagnosis, measurement and verification of diseases status. Therefore, it is an important body fluid to search for novel biomarkers not only to be used as a diagnostic tool, but also to elucidate new molecular pathways involved in diseases and mechanisms explaining altered homeostatic conditions.

Presently, plasma is only collected by invasive techniques. Whereas, plasma is the most important available source for systemic biomarkers obtained by invasive sources, other biological matrices have been explored to screen for biomarkers that are expected to operate at a more local level. Some examples of such alternative biological matrices are tumour tissue, cerebrospinal fluid and suction blister fluid.

The invasive extraction of suction blister fluid is largely derived from the interstitial fluid, which is the place where many important biomarkers are expected to be found. Interstitial fluid (or tissue fluid) is a solution which bathes and surrounds the cells of multicellular animals. It is the main component of the extracellular fluid, which also includes plasma and transcellular fluid. Compared to the very invasive skin biopsies used to analyze local mediators, suction blister fluid is obtained by means which allow less invasive extraction. Invasive suction blister fluid can be used as body fluid to detect small molecules such as glucose and lactate, drugs, study mediators of inflammation, etc. Because suction blister fluid is entrapped inside blisters, it cannot be used in conjunction with a sensor or a plurality of sensors for the continuous detection and/or the continuous monitoring for target molecule(s) since it cannot be in direct contact with any integrated sensor.

On the other hand, skin covers the entire external surface of the human body. Due to its size and accessibility, skin is an attractive target for a variety of applications. Most notably, transdermal route for delivering drugs has potential advantages over other methods of delivery in terms of convenience, non-invasiveness, and reduction of drug degradation. The predominant barrier to transdermal drug delivery is the outermost layer of the skin, the stratum corneum.

The stratum corneum is composed of several densely packed layers of flattened, dead, keratinized cells surrounded by lipid bilayers consisting primarily of ceramides, cholesterol, and free fatty acids. The total thickness of the stratum corneum varies from 10 to 40 µm with an average thickness of 20 µm. This strongly hydrophobic environment inhibits molecular transit of hydrophilic particles/liquids, retarding evaporation of water from the inside and penetration of molecules from the outside. Therefore, the protective function of the skin presents a formidable obstacle and limits the number of drugs that can be delivered transdermally.

Currently, testing one's own glucose concentration is very common and involves a drop of blood taken from the finger tip, which is analyzed via a glucose sensor. This method is not continuous and therefore diabetic people, of type 1 and 2, may experience very often either a state of hypoglycemia or hyperglycemia or both of them many times a day. Moreover, a state of hypoglycemia or hyperglycemia even during a short period of time, but repeated very often, has a disastrous effects on the state of health of the diabetic person. These repeated states might lead in the long term, even if the concentration of glucose is controlled by the abovementioned method, to a deterioration of renal and/or liver functioning and can lead to other deteriorations such as cardiovascular complications. Therefore, new devices which can monitor continuously the concentration of glucose in the body in order to maintain this concentration inside its normal threshold values are much needed.

Presently, there is some breakthrough in this regard in the market. All the technologies available actually are invasive since the sensor is to be placed under the skin and are not very accurate since they need routine calibration and do not last more than a week. This is the case of Navigator® commercialized by Abbott. The Navigator® product is not the only invasive device present in the market, but all of known products lack accuracy, need calibration and do not last for a long period of time. According to the definition of the non-invasive technique, one of the principal requirements is that the sensor should be placed outside the body.

Several patents have proposed that the level of glucose in blood can be monitored by measuring the level of glucose in interstitial fluid. In order to obtain a sample of interstitial fluid, the barrier function of the stratum corneum must be overcome. U.S. Pat. No. 4,775,361, discloses a method of ablating the stratum corneum of a region of the skin of a subject by using pulsed laser light of a wavelength, pulse length, pulse energy, pulse number, and pulse repetition rate sufficient to ablate the stratum corneum without significantly damaging the underlying epidermis. This method should lead to the contact of the sensor with the interstitial fluid. However, its accuracy is very questionable due to the fact that the interstitial fluid is present inside the body under a negative pressure or its movement is restricted, therefore, this kind of method should be comparable to those based on the perforation of the finger in order to obtain a drop of blood.

U.S. Pat. No. 5,423,803, discloses a process for the removal of superficial epidermal skin cells, i.e., stratum corneum, in the human skin. A contaminant having a high absorption in at least one wavelength of light is topically applied to the surface of the skin. Some of the contaminant is forced to infiltrate into spaces between superficial epidermal cells. The treated skin section is illuminated with short laser pulses at the above wave-length, with at least one of the pulses having sufficient energy to cause some of the particles to explode tearing off the superficial epidermal cells. The contaminants include 1 micron graphite particles and the laser used is a Nd:YAG laser. Again, this method should lead to the contact of the sensor with the interstitial fluid. However, its accuracy is very questionable due to the fact that the interstitial fluid is present inside the body under a negative pressure or its movement is restricted, therefore, this kind of method should be comparable to those based on the perforation of the finger in order to obtain a drop of blood.

WO 94/09713 discloses a method for perforating skin comprising the steps of (a) focusing a laser beam in the shape of an ellipse at the surface of the skin with sufficient energy density to create a hole at least as deep as the keratin layer and at most as deep as the capillary layer; and (b) creating at least one hole, each hole having a width between 0.05 and 0.5 mm and a length of equal to or less than 2.5 mm. Again, this method should lead to the contact of the sensor with the interstitial fluid. However, its accuracy is very questionable due to the fact that the interstitial fluid is present inside the body under a negative pressure or its movement is restricted, therefore, this kind of method should be comparable to those based on the perforation of the finger in order to obtain a drop of blood. Another problem associated with this method is the depth of the obtained hole which cannot be controlled therefore leading to the contact of the sensor with the interstitial fluid and the whole blood.

Minimally-invasive methods and apparatus for measuring the glucose level have been produced. For example U.S. Pat. No. 5,730,714 describes a method and a device which uses iontophoresis which employs in this case a constant low voltage and a constant current for as long as the measurement is carried out which may be uncomfortable or at least inconvenient for the subject. EP Patent No. 0889703 describes a method and a device which uses radiation for analyte detection. Both methods described are not accurate since they create an ionic movement in the interstitial fluid near the electrode where the analysis should be carried out. Even if the electrode determines the concentration, it does not represent the same concentration as in the whole interstitial fluid.

Different methods are associated with the transdermal drug delivery. These methods include iontophoresis and electroporation. Thus, one of the possibilities to temporarily breach the barrier function of the skin is by using electroporation, thereby creating aqueous pathways across lipid-based structures of the stratum corneum. Therefore, the electroporation must be repeated on the same part of the skin since the aqueous pathways are reversible and the openings are lost in a very short time. Moreover, the openings are very small in terms of diameter that it is nearly impossible to obtain the interstitial fluid with all of its components and the quantity obtained even with the help of a strong suction is very small if not absent.

Iontophoresis relies on the active transportation of a drug through the skin subjected to an electric field using a simple galvanic current and it is known that iontophoresis typically delivers 100 times less drug quantity than an injection but provides higher local concentrations than oral administration. In iontophoresis, the potential pathways for ingredients to penetrate are restricted, forcing the majority of drugs to permeate the skin via appendageal pores such as hair follicles and sweat glands. These routes only account for about 0.1% of the skin's surface, making drug delivery via iontophoresis inefficient when a large area of tissue requires treatment. Moreover, penetration via the appendages is slow. Moreover, the principle of transdermal drug delivery via iontophoresis relies also on the diffusion of the species from the more concentrated side to the less concentrated side or above the skin. In the case of the interstitial fluid extraction, there is no diffusion which limits largely the flow of the interstitial fluid, due to its presence in the body under a negative pressure comparatively to the blood which is present under a positive pressure, unless a heavy suction is used and the openings are large and permanent.

In contrast, the number of transdermal pathways, available via electroporation, is over 500 times greater than with iontophoresis. In order to improve the absorption of drugs and to defeat the protective qualities of the stratum corneum, iontophoresis device manufacturers sometimes recommend removing the epidermis via microdermabrasion. While this may seem to enhance the permeability, this step is not required with electroporation. Electroporation, also known as electropermeabilization, is a term used to describe the permeabilization of the cell membrane as a consequence of the application of certain short and intense electric fields across the cell membrane, the cells or the tissues.

Electroporation uses high voltage electric perturbation and result in the re-orientation of the lipid layer to form hydrophilic pores or microconduits. High-voltage pulsing has been shown to enhance transport into or across the skin for compounds ranging in size from small ions such as $Na^+$ and $Cl^-$ for example, to moderate sized molecules such as calcein, sulforhodamine, metoprolol, macromolecules such as heparin, oligonucleotides, or latex microspheres of micron dimensions. Again, the principle of transdermal drug delivery via the electroporation relies also on the diffusion of the species from the more concentrated side to the less concentrated side. In the case of the interstitial fluid extraction, there is no diffusion which limits largely the flow of the interstitial fluid unless a heavy suction is used and the openings are large and permanent.

DermaWave No-Needle Mesotherapy System™ uses short, intense electric pulses that alter the electrical potential of the upper layer of the skin and form aqueous pores in the membrane. These pores, or microconduits, are numerous providing the opportunity to deliver compounds evenly into the tissue without the need to alter, change or remove the stratum corneum under only one condition which is the diffusion of the compounds from the more concentrated zone (above the skin) to the less concentrated zone (under the skin). Electroporation proceeds in a domino like manner across the tissue or the upper layer of the skin with the strongest effect being directly beneath the drug application accessory. Some device manufacturers utilize separate accessories for the delivery of electrical pulses and application of topicals. This technique has some problems, since efficient electroporation requires that the electrical energy is delivered in a consistent manner to the tissue with simultaneous delivery of medication. Microconduits return to pre-treatment size after a few milliseconds when the pulses are turned off and the dilation time may be augmented by increasing the duration of the pulsing waveform. However, to achieve maximum transport potential, treatment strategy requires that the applicator is in relatively continuous contact with the tissue area to be treated.

It is disclosed in WO 00/78207 that reverse/reversible electroporation of the skin can be used to have access to a sample of interstitial fluid. Electroporation when carried out using high voltage electric pulse is therefore a very versatile method of reversibly disrupting the stratum corneum. Short pulses (microsecond to millisecond) of pulse field strength sufficient to create a transmembrane potential of more than 0.5 volts cause the capacitive breakdown of the membrane dielectric, leading to transient permeability increases until the membrane recovers sometime after the pulse. Electrically, the skin can be modeled as resistors and capacitors in parallel with most of the resistance residing in the stratum corneum. Thus, if the skin is exposed to an electric pulse, most of the pulse voltage would fall across the stratum corneum, making it the site of the electroporation. Theoretical models of the application of pulsed voltage on the skin suggests that the electropores are created in the lipid lamella and corneocyte membranes such that ions, lipophilic liquid or in general the interstitial fluid with the majority of its components may flow straight through the openings in the stratum corneum if and only if a negative pressure is applied above the treated skin. Therefore, due to the fact that the interstitial fluid has a negative pressure inside the body, it is impossible to drive the interstitial fluid out of the body without the help of a strong suction. Depending on the amplitude of the applied pulse, these electropores might be too small and too uncommon to be detected, being only a few nanometers in diameter and last only a few milliseconds to a few minutes depending on the process of the electroporation.

The openings on the skin obtained by reverse electroporation as described in WO 00/78207 last for a few seconds to a few minutes and the openings have small diameters, in the order of nanometers. Moreover, the reverse or reversible electroporation alone cannot lead to the extraction of interstitial fluid in order to analyze one analyte or a plurality of analytes in the interstitial fluid. Therefore, an enhancement or a combination of enhancements is used to further help the extraction of the interstitial fluid. Such enhancement is described in the art in WO 00/78207 where the electrodes are immersed in different solutions in order to enhance the diffusion of different analytes from the interstitial fluid to the solutions surrounding the electrodes. It is clear that this technique only add more difficulties to analyze one analyte or a plurality of analytes than the difficulties it solves.

Another example of the use of reversible electroporation is the method described in WO 01/62144 where the extraction of the interstitial fluid is carried out by using reverse or reversible electroporation in conjunction with the use of suction. As clearly described in WO 01/62144, the openings do not last for days but for a few minutes at best. Liposomes are thus used to enhance the permeabilization of the skin in WO 01/62144. Moreover, even with the use of liposomes in order to increase the duration of the openings, the openings have small diameters in the order of nanometers and the concentration of the analytes in the extracted interstitial fluid does not reflect those in the interstitial fluid in the body as has been described clearly in WO 01/62144.

It would thus be desirable to be provided with a device that can continuously monitor the concentration of glucose in the body, in a non invasive manner and that can last for a long period of time between calibrations.

SUMMARY

In accordance with the present disclosure, there is now provided a method for non-invasively and continuously extracting interstitial fluid from a subject comprising the steps of irreversibly electroporating the skin; applying a negative pressure at or near the region of the skin irreversibly electroporated for extracting the interstitial fluid; and collecting the extracted interstitial fluid from underneath the opened epidermis.

The method described herein can also be used for the electro-suturing of the skin.

In accordance with the present disclosure, there is now also provided a device for non-invasively and continuously extracting interstitial fluid from the skin of a subject comprising means for irreversibly electroporating the skin by generating a non pulsed voltage and a pulsed voltage between at least one first moving or stationary electrode and a second stationary electrode; a vacuum pump providing a negative pressure above the skin; and a collecting chamber for collecting the interstitial fluid extracted from the skin.

In an embodiment, the method also comprises the step of analyzing the concentration of an analyte or a plurality of analytes in the interstitial fluid extracted from the skin.

In another embodiment, a non-pulsed voltage and a pulsed voltage are generated between at least a first moving or stationary electrode and a second stationary electrode for irreversibly electroporating the skin.

In a further embodiment, the analyte is glucose.

In a further embodiment, a negative pressure against the atmosphere is applied in order to extract the interstitial fluid.

In an embodiment, the method also comprises the step of transmitting the analysis of the concentration of the analyte in the extracted interstitial fluid from underneath the opened epidermis.

In another embodiment, the collecting of the interstitial fluid and the analyzing of the concentration of the analyte in the extracted interstitial fluid are regulated by a check valve, such as for example but not limited to, a one-way valve In an additional embodiment, the negative pressure is pulsed or continuous.

Further, the negative pressure applied at or near the region of the skin irreversibly electroporated can be monitored by a pressure sensor.

In another embodiment, the subject is an animal or a human.

In a further embodiment, the collecting chamber comprises an extraction chamber for collecting the interstitial fluid extracted from the skin.

In another embodiment, the at least one first and second electrodes are contained in the collecting chamber or outside the chamber.

In an additional embodiment, the extraction chamber is a separate part from the first and second electrodes used for the irreversible electroporation.

In an embodiment, the device further comprises a biosensor or a plurality of sensors for analyzing the concentration of an analyte or a plurality of analytes in the extracted interstitial fluid from underneath the opened epidermis.

The biosensor or the plurality of sensors can comprise an electrochemical sensor or an optical sensor; a wired or wireless communication device; a sensing electrode, a reference electrode and a counter electrode; and/or a sensing electrode and an accompanying electrode acting both as a reference and a counter electrode.

In a further embodiment, the biosensor or a plurality of sensors continuously analyzes the concentration of glucose in the interstitial fluid extracted from underneath the opened epidermis.

In an embodiment, the device further comprises an adhesive means for fixing the device on the skin of the subject, such as a bracelet, a strap or a combination thereof.

In an embodiment, the device further comprises a pressure sensor for monitoring the pressure applied on the skin.

In another embodiment, the device further comprises a temperature sensor for monitoring the temperature of the extracted interstitial fluid.

In an embodiment, a valve is disposed between the biosensor and the collecting chamber creating a discontinuity between the extracted interstitial fluid and the interstitial fluid being analyzed by the biosensor.

In an embodiment, the pump is a peristaltic pump, a diaphragm pump, or a piston pump.

In another embodiment, the biosensor comprises a Bis(2, 2-bipyridyl)dichloro Osmium(II), complexed with poly(1-vinylimidazole) mediator in conjunction with a dispersed electronic conductor.

In an embodiment, the device further comprises a sampling chamber connected to the extraction chamber by a pumping conduit, the sampling chamber collects the extracted interstitial fluid from the skin for its analysis.

In another embodiment, the sampling chamber is continuously sealed by a septum connected to the sampling chamber.

In another embodiment, the device further comprises a microcontroller connected to the pressure sensor in order to monitor and control the pressure above the skin and inside the extraction chamber.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims

FIG. 2A is a cross-sectional side view of an alternate embodiment of the device of the present disclosure connected to the skin;

FIG. 2B is an enlarged view of the encircled region 2B-2B seen in FIG. 2A showing the output extraction channel connected to the check valve of the alternate device;

FIG. 3A is a bottom plan view of the device showing an example of the electrodes configuration;

FIG. 3B is a cross-sectional side view along line 3B-3B of the electrodes configuration of the device shown in FIG. 3A.

DETAILED DESCRIPTION

Figure 1A:
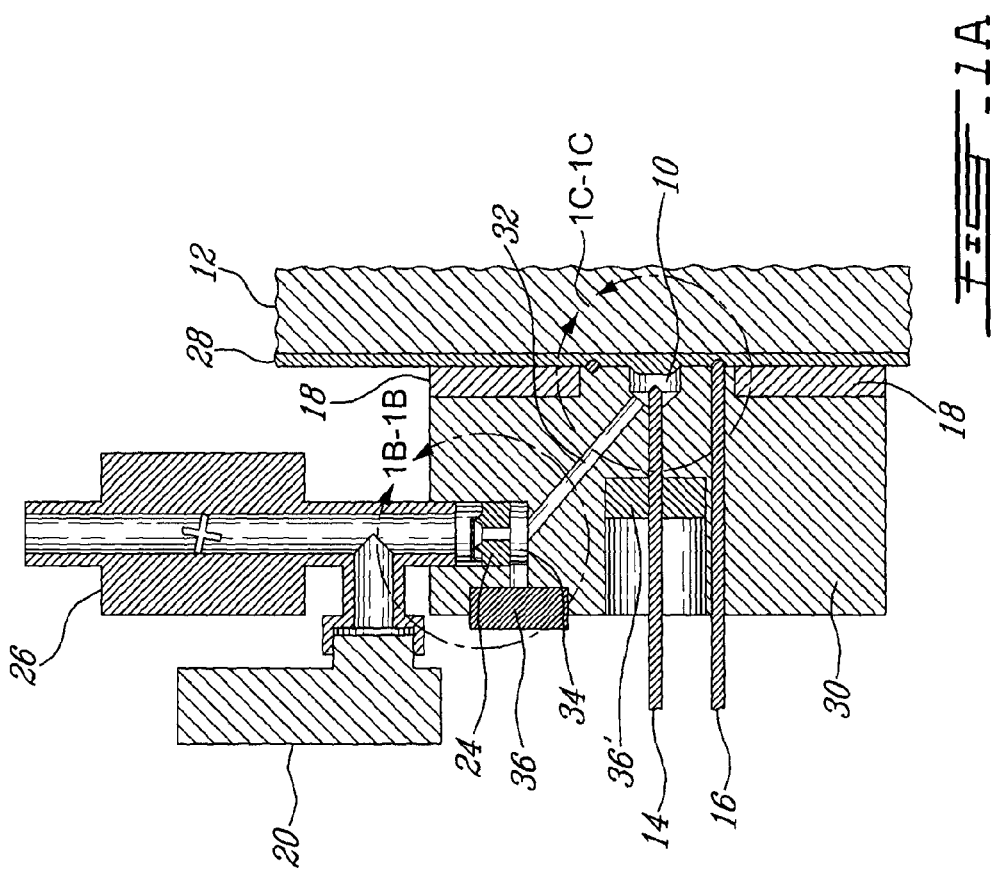
FIG. 1A is a cross-sectional side view of the device of the present disclosure connected to the skin.

There is provided herein a device for obtaining continuously and over long periods of time a sufficient quantity of interstitial fluid from the human body in a non-invasive way. The method and device disclosed herein consists in the combination of irreversible electroporation of human skin and suction of the interstitial fluid through the permeabilized and the micro-opened skin. By irreversible electroporation described herein, we refer to the method which leads to a permanent opening as long as the suction is applied. Moreover, by a sufficient quantity of interstitial fluid described herein, we refer to the optimized and needed quantity of interstitial fluid for the continuous monitoring even if this quantity can be increased by increasing the number of openings and by increasing the negative pressure and alternately decreased by reducing the negative pressure inside the chamber and reducing the quantity of the openings.

Irreversible electroporation, or the ability of certain electrical pulses to permanently permeabilize the cell membrane, is used primarily for ablation of microorganisms and cells in vitro and studied only as an upper limit of electrical parameters for reversible tissue electroporation applications. The various applications of reversible electroporation require cells to survive the procedure and therefore the occurrence of irreversible electroporation, following which cells die, is obviously undesirable. Therefore, irreversible electroporation is viewed as an undesirable side effect and is studied only to define the upper limit of electrical parameters that induce reversible electroporation (Rubinsky, 2007, Technology in Cancer Research and Treatment, 6: 255-259).

The present disclosure describes a method for the non invasive and continuous extraction of the interstitial fluid through the skin. This method as will be seen hereinafter provides an accurate way to obtain openings that last for days or as long as the monitoring of an analyte or a plurality of analytes in the interstitial fluid is carried out. The openings according to the present disclosure are in the order of micrometers, which is different than what is described in the actual art in the order of nanometers. Moreover, the effectiveness of the method described in the present description has been verified by applying it on five human volunteers with one of them being a diabetic of type 2. The electroporation as described in the present disclosure is an irreversible electroporation which lead to irreversible openings of the skin or the epidermis. The openings last for days, hence, an accurate and precise monitoring of one or a plurality of analytes in the extracted interstitial fluid can be carried out with and without further electroporation of the same area of the skin. The present disclosure provides the application of a non-pulsed DC voltage as explained hereinbelow between the electrodes at a fixed current at the same time of the applications of the pulsed voltage necessary for the irreversible electroporation and between the pulses.

Figure 1C:
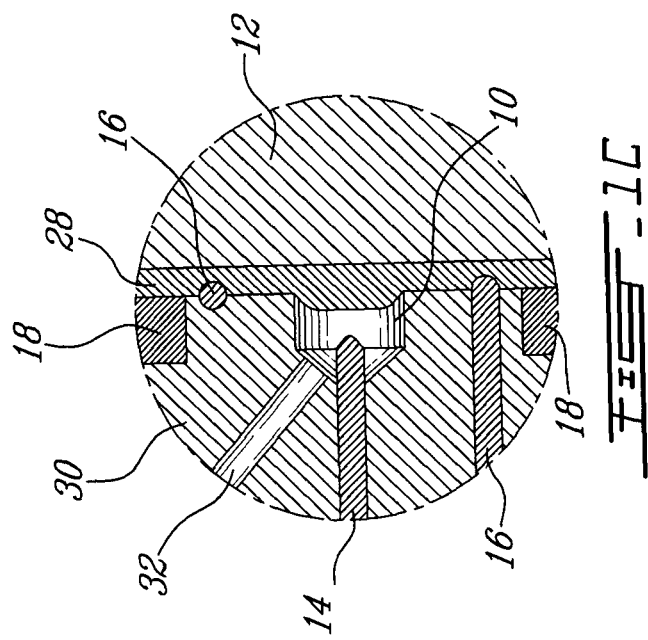
FIG. 1C is an enlarged view of the encircled region 1C-1C seen in FIG. 1A showing the extraction chamber of the device connected to the skin comprised in the device.
Figure 1B:
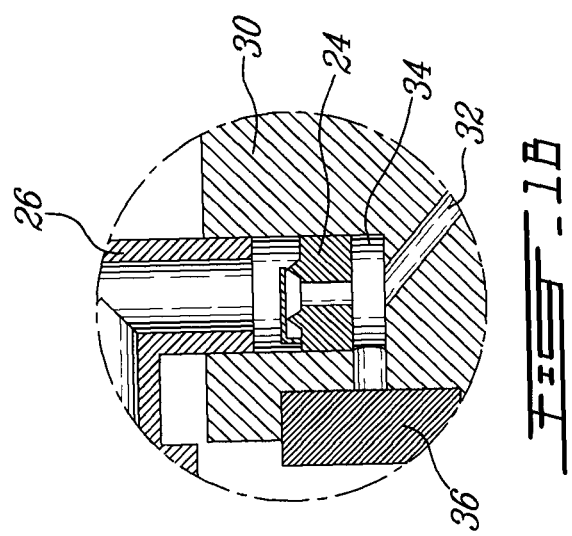
FIG. 1B is an enlarged view of the encircled region 1B-1B seen in FIG. 1A showing the check valve creating discontinuity between the analyzed fluid and the freshly extracted fluid in the sampling chamber comprised in the device.

An embodiment of the device encompassed herein is illustrated in FIG. 1, showing a typical application of the method and is designed to be used for occasional or continuous sampling of the extracted transdermal fluid. The sampling method could be manual or automated. The device comprises an insulating body 30 maintained in contact with the skin 12 through the epidermis 28 using an adhesive or any other suitable sealing product or maintaining method 18. The contact of the body 30 with the epidermis 28 comprises mainly one opening constituting the primary extraction chamber 10. The extraction chamber 10 allows passage for at least one excitation electrode 14 and a pumping conduit 32.

The extraction chamber 10 can be made completely from a polymeric material, a combination of a polymeric material or any other material that are electrically conductive or insulating. The device can be covered by a material in order to facilitate its use in a swimming pool, during the use of a bath or a shower and/or any situation where a liquid can surround the extraction chamber 10. The extraction chamber 10 can include a sealed hole so that the collected freshly extracted fluid can be analyzed remotely from the device. Furthermore, in order to increase the fixture of the extraction chamber 10 as described herein, a non allergenic material such as a bracelet or a strap can be used to stabilize the contact between the device and the skin 12.

Before the application of the extraction chamber 10 on the skin 12, the skin 12 can be gently cleaned by any known chemicals used in medicine to clean such skin 12 or simply by the use of a soap and/or water. Preferably, any chemicals that evaporate after cleaning are used such that they do not leave any residue at the surface of the skin 12. Moreover, the chemicals or the soap should not induce any allergenic reaction of the skin 12 nor modify the structure of the skin 12. As soon as the skin 12 is gently cleaned, the extraction chamber 10 is attached on the top of the cleaned skin 12 by the help of the non allergenic material such as the adhesive 18 or the strap or bracelet.

The preferred part of the skin 12 is any part of the skin covering the arm of a person but the majority of the body skin can be used with the device and the method described herein.

The pumping conduit 32 is in contact with a sampling chamber 34 where the chosen sampling device shall be able to collect samples of the extracted transdermal fluid. The collection can be carried out, for example through a septum 36 which allows for continued sealing of the sampling chamber 34. The sampling chamber 34, pumping conduit 32 and extraction chamber 10 are isolated from a pump 26 for example by a check valve or a one-way valve 24, thus creating a discontinuity between the analysed fluid and the freshly extracted fluid which is to be analysed. The check valve 24 can be any means that creates or help to achieve a discontinuity between the analyzed fluid and the freshly extracted fluid. The extraction is continuously carried out by the application of a controlled negative pressure that is applied in the conduit system comprised namely of the extraction chamber 10, the extraction or the pumping conduit 32 and the sampling chamber 34. The controlled negative pressure is maintained by the action of the pump 26 and the level of the negative pressure is continuously monitored and controlled using a pressure sensor 20 or pressure switch, which could be located before or after the check valve 24.

The negative pressure is attained by activating the pump 26 in an on/off fashion or in a continuously modulated fashion. The actual value of the negative pressure can be controlled by the use of the pressure sensor 20 or a pressure switch. The pump 26 and the pressure sensor 20 can be under the control of a microcontroller (FIG. 4) that shall continuously or discontinuously monitor the actual pressure in the device from reading the actual status of the pressure sensor 20 or the pressure switch and shall accordingly activate or deactivate the operation of the pump 26 in a continuous, discontinuous or modulated fashion in order to achieve the desired negative pressure. A temperature sensor can also be incorporated in order to improve the efficiency of the device and to correct the reading of the biosensor 22 or the plurality of biosensors if needed.

The vacuum is generated inside the chamber 10 between the skin 12 and the pump 26 in order to improve the adhesion, the continuous extraction of the transdermal fluid, the circulation of the extracted fluid and, consequently, the continuous monitoring of one analyte or a plurality of analytes in the extracted fluid. Preferably, the vacuum pump 26 is capable of providing a vacuum that will provide sufficient suction to stretch the portion of the skin in the region from which the sample of interstitial fluid is to be extracted. As the suction provided by the vacuum pump 26 is stretching the appropriate portion of the skin, the suction provided by the vacuum pump 26 also causes the stretched portion to become completely filled with interstitial fluid. A vacuum pump 26 that is suitable for the device defined herein can be a peristaltic pump, a diaphragm pump, a piston pump, a rotary vane pump, or any other pump that will perform the required functions set forth previously. Typically, the vacuum pump 26 preferably employs a self-contained permanent magnet DC motor. Vacuum pumps that are suitable for this invention are well-known to those of ordinary skill in the art and are commercially available. The vacuum provided by the vacuum pump 26 can be continuous or pulsed. A continuous vacuum is preferred for the reason that it requires fewer components than does related to a pulsed vacuum. It is preferred that the applied vacuum does not cause irreversible damage to the skin. It is preferred that the applied vacuum does not produce bruises and discolorations of the skin that persist for several days. It is also preferred that the level of applied vacuum and the duration of application of the vacuum do not be so excessive that it causes the dermis to separate from the epidermis, which results in the formation of a blister filled with fluid.

The irreversible electroporation of the skin is carried out by the application of a pulsed voltage between two electrodes (14, 16) or a plurality of electrodes forming a network of electrodes. As an illustration of the art herein, the excitation part of the process is carried out by the use of at least two electrodes 14 and 16 one electrode 16 may be stationary and in continuous contact with the epidermis 28. One of the excitation electrodes 14 may or may not be maintained in contact with the epidermis 28. The electrode 14 may be moved on and off the epidermis 28 by a mechanical motion that may be carried out through the sealing septum 36.

The target result of the irreversible electroporation herein is an effective electropermeabilization of the epidermis 28 non-invasively, with permanent opening(s) as long as the suction is applied, without any pain felling and which can permit a continuous transdermal fluid extraction for a time as long as needed. Herein, the transdermal fluid is the interstitial fluid. A continuous fluid extraction is intended herein to refer to a continuous flow of the interstitial liquid through the skin 12, including the opening(s) in the epidermis 28, into the extraction chamber 10.

As described herein, the irreversible electroporation is done by varying and actuating different parameters which include: a non-pulsed floor DC voltage ($V_F$/V), the intensity of the current flowing between the electrodes through the skin 12 (I/mA), the amplitude of the pulsed applied voltage ($V_A$/V), the period of the pulses (ms), the duty cycle (%) and the duration time (s). The non-pulsed floor DC voltage can be defined as the minimum value of the pulsed voltage before and between the pulses. This voltage can be applied at the same current intensity a few seconds before the pulses or immediately at the starting of the irreversible electroporation. Table 1 shows the typical values associated with all the above different parameters. Herein, $V_F$ is the non-pulsed voltage applied between the electrodes (14, 16) before and between the pulses and its value can vary between 0 to the value of the pulsed applied voltage, I is the intensity of the current either constant or variable, $V_A$ is the value of the applied pulsed voltage which has a value that can be comprised between a few volts to hundreds of volts and minimal value is $V_F$, and the remaining parameters have the usual signification.

TABLE 1

Preferred parameters associated with the irreversible electropermeabilization of the skin.

| Parameters | Preferred Values |
| --- | --- |
| $V_F$ (Volt) | 0 to $V_A$ |
| $V_A$ (Volt) | $V_F$ to 1000 V |
| I (mA) | 0.001 to 1000 |

TABLE 1-continued

Preferred parameters associated with the irreversible electropermeabilization of the skin.

| Parameters | Preferred Values |
|---|---|
| Period (ms) | 0.01 to 50 |
| Duty cycle (%) | 0.001 to 100 |
| Duration time (s) | 5 to 3600 |
| Distance between the electrodes (mm) | 0.01 to 20 |

Figure 2D:
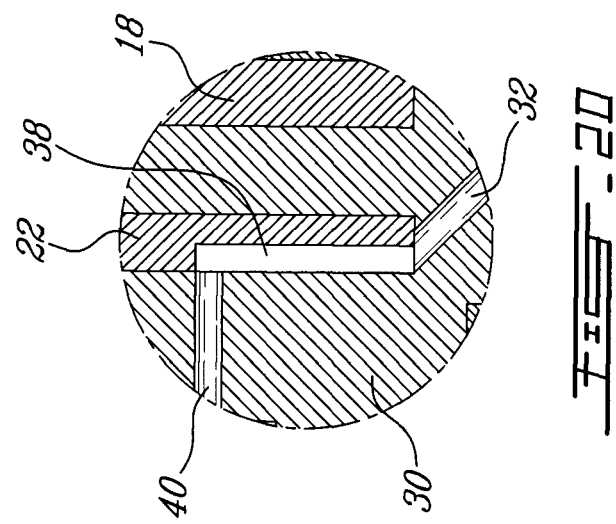
FIG. 2D is an enlarged view of the encircled region 2D-2D seen in FIG. 2A showing the biosensor and the measurement chamber comprised in the alternate device.
Figure 2C:
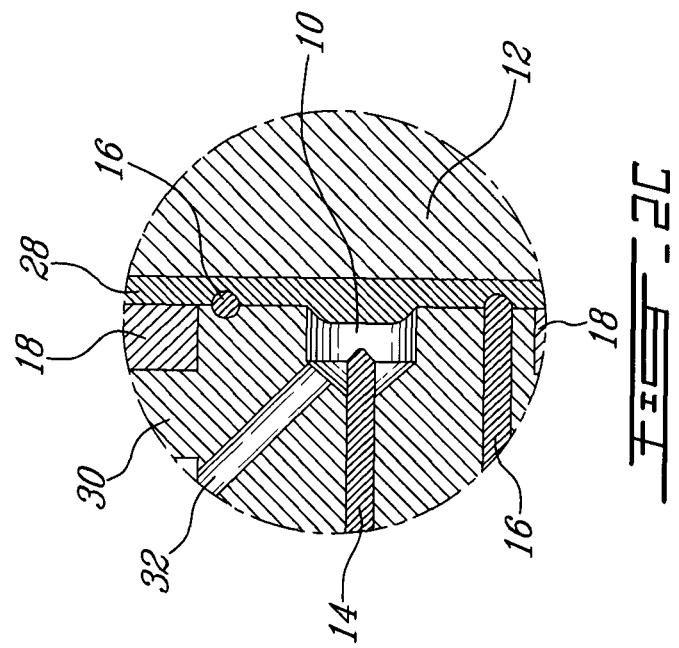
FIG. 2C is an enlarged view of the encircled region 2C-2C seen in FIG. 2A showing the extraction chamber of the alternate embodiment when connected to the skin.

In an alternate embodiment of the device as illustrated in FIG. 2, the extraction chamber 10 allows the passage for at least one excitation electrode 14 and a pumping conduit 32. The pumping conduit pass through a measurement chamber 38 where the extracted transdermal fluid may be analysed by a biosensor or a plurality of biosensors 22. The sampling chamber 34, the pumping conduit 32, the measurement chamber 38 and the output extraction channel 40 are isolated from the pump 26 by for example a check valve or one-way valve 24, thus creating a discontinuity between the analysed fluid and the freshly extracted fluid which is to be analysed.

The electrodes (14, 16) may be commercially available. These electrodes should by their form and installation minimise the depth of the electric field and thus decrease the risk of stimulating nerves in the skin and therefore making the process painless. The electrodes 14 and 16 herein are made from any electrically conductor materials and preferably noble metal conductors, either alloyed or not. The extremity of the electrodes (14, 16) can have any form. Moreover, herein, some of the electrodes (14, 16) can have a small diameter. The distance, the configuration, the diameter and the form of the two electrodes (14, 16) can vary as long as they do not affect the target result of the irreversible electroporation. The selection of the suitable proprietary electrodes (14, 16) is well within the scope of the person skilled in the art.

FIG. 3 describes an example of the electrodes 14 and 16 configuration in the excitation section of the device. For example, the stationary electrode 16 may have a circular shape and may also be located around the location of the electrode 14. Electrode 16 may be affixed onto the surface of the body 30.

Figure 4:
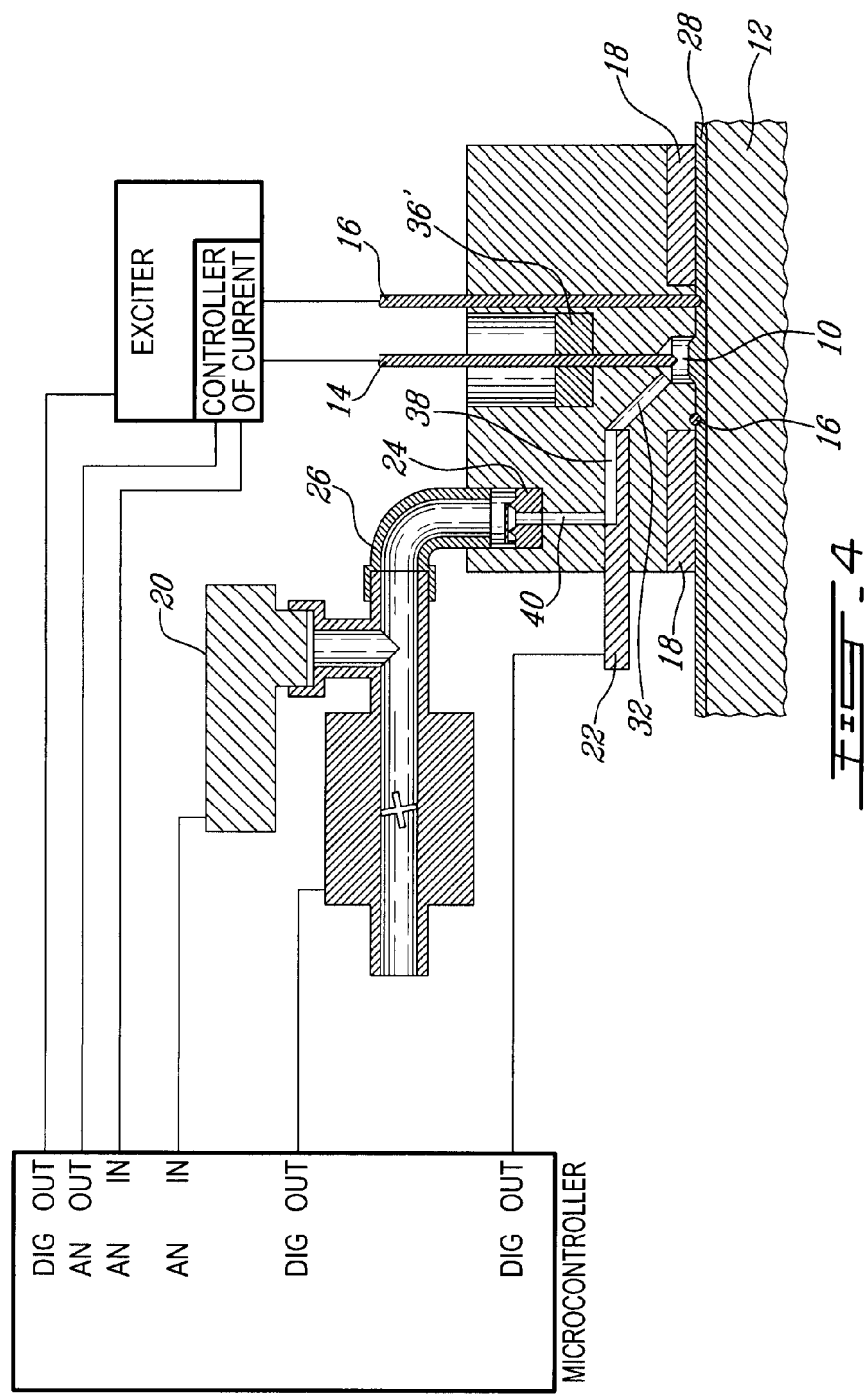
FIG. 4 is a cross-sectional side view of the device of the present disclosure connected to the skin and to a microcontroller.

FIG. 4 describes an example of the control structure that is part of the excitation and extraction process for the transdermal fluid. The excitation and the extraction parts of the device can be controlled by a microcontroller in continuous or discontinuous fashion in order to allow the processes to be initiated and maintained for accessing the transdermal fluid.

The microcontroller can also control the application of the electrical excitation on the skin 12. If required, the mechanical contact of the electrode 14 with the skin 12 could be controlled by the microcontroller. Once the contact is established between the electrodes 14 and 16 with the epidermis 28, the microcontroller then starts the process of the irreversible electroporation of the skin. The microcontroller shall be able to control over the time the voltage either the pulsed applied voltage or the non pulsed floor voltage, the current, the repetition rate, the pulse duration or the duty cycle of the pulses, the duration of application of the voltages and/or currents, the measurement of the voltages and the currents and the control of the conditions that may direct the starting and/or stopping of the application of the voltages and the currents.

Also encompassed is the reading and the analysis of the signal obtained from the biosensor or a plurality of sensors 22 in order to transform the information and send the information to an alarm or a cell phone, for example, for further diffusion of the obtained information. The sent information can have many meanings such as the concentration of the analyte or the plurality of the analytes, a decision that the concerned person should take or simply a warning.

When the biosensor 22 for the continuous monitoring of glucose is based on the electrochemical methods, it can comprise three or two electrodes. In the case of three electrodes configuration, the first electrode is a common Ag/AgCl reference electrode; an inert counter-electrode constitutes the second electrode; and the third electrode is the sensing electrode. The sensing electrode comprises an inert electronic layer surrounded by a sensing layer. The sensing layer is obtained by the deposition of a homogenous mixture of a glucose oxidoreductase enzyme such as glucose oxidase, a mediator, a nano/micro powder of an electronic conductor, a cross-linking agent, a hydrophilic material, a hydrophilic additive and an adhesion promoter on the electronic layer based sensing electrode.

The term "inert" is used herein with the meaning that the referred material is stable chemically, electrochemically, mechanically and does not interfere with the target reaction.

When the biosensor 22 is based on electrochemical methods, it can comprise a polymeric and electronically non conducting protection layer which can cover and protect the reference electrode, the sensing electrode, and the counter electrode from the irreversible adsorption/absorption of chemical species or more generally against the alteration of their nature and original characteristics.

Alternatively, any sensing element known in the art can be used to determine the presence or the amount of at least one analyte of interest and the particular features of the sensing element being part of the biosensor 22 are not critical to the invention. The biosensors 22 herein refer to those based on electrochemical, chemical, biochemical and optical methods. Thus, any analyte detection method, sensor, or system suitable for use with the analyte of interest, for example optical or electrochemical sensors known in the art, may be used in the biosensor 22, such as for example an interference-free biosensor known in the art. One example is the use of enzyme electrodes based on Bis(2,2-bipyridyl)dichloro Osmium(II), complexed with poly(1-vinylimidazole) as a mediator. The signal generated by the biosensor 22 or the plurality of biosensors could be read for example by a microcontroller and stored or displayed for usage by the user. The data could be eventually accessible for review by any visual or electronic data transfer means, having a direct connection or a radio connection and/or optical connection or other available data connection means. The biosensor 22 disclosed herein can comprise an electrochemical sensor, a hydrogel layer, a potentiostat and a wired or wireless communication device for example. The biosensor 22 can be removable from the device such that it can be manipulated and placed elsewhere independently from the rest of device.

One example of an analyte that can be monitored by the device disclosed herein, with a biosensor or electrochemical sensor 22, is glucose. Many analytes could be monitored in this liquid. The device disclosed herein allows continuous monitoring of an analyte value over a long period of time. More specifically, a continuous monitoring is intended to be directed to a monitoring of an analyte at multiple time in a day or hours instead of a punctual monitoring as done by means known in the art.

In the case of glucose, the biosensor 22 disclosed herein has a sensing layer on a sensing electrode, a reference and a counter electrode. The sensing layer is obtained by the deposition on the sensing electrode of a homogenous mixture of a glucose oxidoreductase enzyme, such as glucose oxidase, a mediator, a nano/micro powder of an electronic conductor, a cross-linking agent, a hydrophilic material, a hydrophilic additive and an adhesion promoter. A positive or anodic potential corresponding to the oxidation potential of the metallic ion in the mediator is applied and the obtained currents are converted to different values representing the glucose concentrations by an electronic interface. The current obtained and converted can be displayed locally and/or transmitted remotely to different parties through telemedicine networks for example, along with pertinent data such as the date and time of the reading, the GPS location of the patient, etc. for example, and depending on the value of the reading, alerts could be configured to be broadcasted to different parties by different media means. In an embodiment, the biosensor 22 consists of an electrochemical glucose sensor, a hydrogel layer, a potentiostat that can be connected to a wired or wireless communication device, such as for example but not limited to a wired or wireless communication device. It should be clarified herein that any commercially available sensor that can detect continuously the target analyte in the continuously extracted interstitial fluid can be used without restriction according to this invention.

Table 2 shows some analytes that can be found, and thus monitored, in the extracted interstitial fluid, which constitute a subject of the current disclosure, and their related diseases.

TABLE 2

List of some molecules, some proteins and some hormones found in the interstitial fluid.

| SM/(P)/(H) | Disease(s) |
|---|---|
| Glucose | Diabetes |
| Lactate | Trauma |
| Cortisol | Stress |
| Triglyceride | Atherosclerosis, heart disease and stroke |
| Cholesterol | Atherosclerosis |
| Low-density lipoprotein | Cardiovascular diseases |
| High-density lipoprotein | Cardiovascular diseases |
| Amyloid P component | Beta-2-microglobulin amyliodosis/liver associated |
| Beta-2-microglobulin | Psorlasis |
| C-reactive protein | Muscle strength loss/cancer/psoriasis/cardiovascular |
| S100A7 (psoriasin) | Psoriasis/Skin cancer |
| Cartilage oligomeric matrix protein | Arthritis |
| Clusterin | Heart disease/Infarction related and diabetes/liver associated/squamous cell carcinoma |
| Colony stimulating factor 1 | Endometrial adenocarcinoma |
| Complement component C5a | Cardiovascular related |
| Complement component H | Bladder cancer |
| Cystatin A | Malignancy in human epidermal keratinocytes |
| Cystatin C | Renal function |
| Ezrin | Skin tumour related |
| GST Pi | Skin tumour related |
| Haptoglobin related protein | Malignant lymphoma |
| Hepatocyte growth factor activator | Prostate cancer |
| Histidine-rich glycoprotein | Alzheimer's disease |
| IGF-binding protein 3 | Liver disease/tiredness in highly trained sportsmen |
| Interleukin-18 | Coronary artery disease and diabetes/gastric cancer/HIV related/kidney related/ovarian cancer/psoriasis/graft-versus-host disease/breast cancer related/cardiovascular related/lung disease related |
| Interleukin-1 receptor entagonist protein | Psoriasis/gynaecological cancers/heart transplant and bypass related/psoriatic arthritis related |
| Interleukin-6 signal transducer (gp130) | Heart Failure related/HIV infection/tumour related/scleroderma/chronic renal failure/fibromyalgia/inflammatory disorders of the skin |
| Insulin-like growth factor binding protein-4 | Chronic renal failure |
| Acid-labile subunit insulin-like GF | Growth disorders |
| Lipopolysacharide-binding protein | Bacterial infection in cirrhotic patients |
| Orosomucoid | Bladder cancer/cardiovascular related |
| Paraoxonase 1 | Liver function monitoring after transplantation/vascular dementia |
| Periostin | Bone metastases from breast cancer |
| Phosphoglycerate kinase 1 | Pancreatic ductal adenocarcinoma |
| Phospholipid transfer protein | Accelerated atherosclerosis in type 2 diabetes/coronary heart disease |
| Prostaglandin D2 synthase | Perilymphatic fistula/CSF leakage and related/diabetes/hydrocephalus |
| Protein Z | Ischaemic stroke |
| Amyloid A | Adipose related inflammation |
| Sex hormone-binding globulin | Bone fracture risk in men/insulin resistance in obese males/cardiovascular mortality in elderly men |
| Thioredoxin | Oxidative stress in patients with rheumaloid arthritis/skin cancer related |

The present disclosure will be more readily understood by referring to the following examples which are given to illustrate the embodiments rather than to limit its scope. In the following Example I, the average flow depends on the number of openings and the amplitude of the vacuum. The rate of the average flow obtained herein is an example related to the specific values of the other parameters used in this example.

EXAMPLE I

Irreversible Electroporation and Suction of Interstitial Fluid

In order to irreversibly electroporates the skin, a 6V non-pulsed floor DC voltage ($V_F$) at 0.13 mA is applied between the electrodes maintained mechanically at the surface of the skin before and between the applied pulsed voltage. The applied pulsed voltage between the electrodes has a frequency equal to 0.25 ms, a duty cycle equal to 1% and an applied current equal to 0.13 mA. The amplitude of the pulsed voltage is 66 V and its minimum value is equal to $V_F$ comparatively to the ground and the duration of the electroporation is 240 s. The average flow rate of the obtained interstitial fluid at 30 kPa of negative pressure 7 µl/min. The duration of the opening was estimated to last 3 weeks without repeated irreversible electroporation. In the same experiment, the extraction of the interstitial fluid at the same conditions was carried out successfully at 10 kPa negative pressure relative to the atmosphere.

The analysis of three analytes in the continuously extracted transdermal fluid from a diabetic Type 2 subject by the analytical methods used in hospital laboratories is shown in Table 3.

TABLE 3

Analyte concentrations in the extracted transdermal fluid from a diabetic type II.

| Analytes | Concentration (g/l) |
| --- | --- |
| Glucose | 1.46 |
| Triglycerides | 0.89 |
| Cholesterol | 0.55 |

EXAMPLE II

Preparation of Bis(2,2-bipyridyl)dichloro Osmium(II), Complexed with poly(1-vinylimidazole) Mediator Based Glucose Sensing Electrode The polymerization of poly(1-vinylimidazole) is carried out by heating 12 ml of 1-vinylimidazole and 1 g of 2,2'-azobis(1-Cyano-1-methylethane) at 70° C. for 2 h under argon atmosphere. A dark yellow precipitate is formed soon after heating. After the reaction mixture is allowed to cool, the precipitate is dissolved in methanol and added drop wise to a strongly stirred solution of acetone. The filtered precipitate of poly(1-vinylimidazole) is a pale yellow hygroscopic solid. Bis(2,2-bipyridyl)dichloro Osmium(II) (Os(bpy)2Cl) complexed with poly(1-vinylimidazole) is prepared by mixing 0.3 mole of Os(bpy)2Cl and 3 mmole of poly(1-vinylimidazole). The mixture is heated at reflux in 225 ml of ethanol:water 1:1 in the dark for 8 days. The Os(bpy)2Cl complexed with poly(1-vinylimidazole) is recovered by solvent stripping and subsequent dissolution in methanol, followed by precipitation into diethyl ether and vacuum drying.

Preparation of the Sensing Layer

In order to improve the performance of the sensing layer, an electronic nano/micro conductor powder, an electrophilic additive and an adhesion promoter are added to the mixture used to prepare the sensing layer. The preferred electronic conductor is carbon such as Vulcan® XC72R and its preferred percentage in the sensing layer is comprised between 0.005% and 2% (WAN) and more preferably is equal to 0.01%. However, any other electronic conductor known in the art could be used as long as it is stable chemically, electrochemically and its particles dimensions are in the order of nanometers to a few micrometers. The preferred electrophilic and adhesion promoter that it is used is (3-aminopropyl)trimethoxysilane or any derivative of silane. The preferred percentage of the electrophilic and adhesion promoter in the sensing layer is between 0.001 to 5% (W/W) and more preferably 0.1%. The preferred method to prepare the sensing layer is by mixing 2 µl aliquot of 5 mg/ml of Os(bpy)2Cl complexed with poly(1-vinylimidazole) in an alcoholic solvent, 2 µl of a glucose oxidase (at a concentration of 4 mg/ml or more) in an isotonic or simply a phosphate buffered solution (ph≅7.0), 1.2 µl of a 2.5 mg/ml solution of Peg™400, the Vulcan® XC72R (0.01% W/W) and the (3-aminopropyl)trimethoxysilane (0.1% W/W). The mixture is quickly stirred and dropped on the surface of the electronic conductor (sensing electrode) and, finally, allowed to dry for at least 24 h preferably under vacuum.

While the invention has been described with particular reference to the illustrated embodiment, it will be understood that numerous modifications thereto will appear to those skilled in the art.

Accordingly, the above description and accompanying drawings should be taken as illustrative of the invention and not in a limiting sense.

In the foregoing description, certain terms have been used for brevity, clearness, and understanding. No unnecessary limitations are to be implied therefrom beyond the requirement of the prior art because such terms are used for descriptive purposes and are intended to be broadly construed.

What is claimed is:

1. A method for non-invasively and continuously extracting interstitial fluid from a subject comprising the steps of:
   electroporating the skin by applying a non-pulsed floor voltage 4 volt to 8 volt at a current intensity between 0.1 mA to 0.25 mA before and during an applied pulsed voltage comprised between 20 volt to 90 volt at a current intensity between 0.1 mA to 0.25 mA for a two electrodes configuration;
   applying a negative pressure at or near the region of the skin being electroporated, the simultaneous combination of electroporating the skin and applying the negative pressure forming openings in the skin for extracting the interstitial fluid, the interstitial fluid being extractable only so long as the negative pressure is applied in combination with electroporating the skin; and
   collecting the extracted interstitial fluid from the skin.

2. The method of claim 1, further comprising the step of analyzing the concentration of an analyte or a plurality of analytes in the interstitial fluid extracted from the skin.

3. The method of claim 1, wherein a non-pulsed voltage and a pulsed voltage are generated between at least a first moving or stationary electrode and a second stationary electrode for electroporating the skin.

4. The method of claim 2, wherein the analyte is glucose.

5. The method of claim 1, wherein said negative pressure is about 2 kPa to about 98 kPa.

6. The method of claim 2, further comprising the step of transmitting the analysis of the concentration of the analyte in the extracted interstitial fluid from the skin.

7. The method of claim 2, wherein the collecting of the interstitial fluid and the analyzing of the concentration of the analyte in the extracted interstitial fluid are regulated by a check valve.

8. The method of claim 1, wherein the negative pressure is pulsed or continuous.

9. The method of claim 1, wherein the negative pressure applied at or near the region of the skin is monitored by a pressure sensor.

10. The method of claim 1, wherein the subject is an animal or a human.

11. The method of claim 7, wherein the check valve is a one-way valve.

12. A device for non-invasively and continuously extracting interstitial fluid from the skin of a subject comprising:
an electroporator generating a non-pulsed floor voltage 4 volt to 8 volt at a current intensity between 0.1 mA to 0.25 mA before and during an applied pulsed voltage comprised between 20 volt to 90 volt at a current intensity between 0.1 mA to 0.25 mA between at least one first moving or stationary electrode and a second stationary electrode for electroporating the skin;
a vacuum pump providing a negative pressure above the skin, the vacuum pump in operation providing the negative pressure simultaneously with electroporating the skin to form openings in the skin for extracting the interstitial fluid, the interstitial fluid being extractable only so long as the negative pressure is applied in combination with electroporating the skin; and
a collecting chamber for collecting the interstitial fluid extracted from the skin.

13. The device of claim 12, wherein said collecting chamber comprises an extraction chamber for collecting the interstitial fluid extracted from the skin.

14. The device of claim 12, wherein said at least one first and second electrodes are contained in the collecting chamber.

15. The device of claim 13, wherein the extraction chamber is a separate part from the first and second electrodes used for the electroporation.

16. The device of claim 12, further comprising a biosensor or a plurality of sensors for analyzing the concentration of an analyte or a plurality of analytes in the extracted interstitial fluid from the skin.

17. The device of claim 16, wherein the biosensor or the plurality of sensors comprise an electrochemical sensor or an optical sensor.

18. The device of claim 16, wherein said biosensor or a plurality of sensors further comprise a wired or wireless communication device.

19. The device of claim 16, wherein said biosensor or plurality of sensors comprise a sensing electrode, a reference electrode and a counter electrode.

20. The device of claim 16, wherein said biosensor or plurality of sensors comprise a sensing electrode and an accompanying electrode acting both as a reference and a counter electrode.

21. The device of claim 16, wherein said biosensor or a plurality of sensors continuously analyzes the concentration of glucose in the interstitial fluid extracted from the skin.

22. The device of claim 12, wherein said device further comprises an adhesive means for fixing the device on the skin of the subject.

23. The device of claim 22, wherein said adhesive means is a bracelet, a strap or a combination thereof.

24. The device of claim 12, wherein said device further comprises a pressure sensor for monitoring the pressure applied on the skin.

25. The device of claim 12, wherein said device further comprises a temperature sensor for monitoring the temperature of the extracted interstitial fluid.

26. The device of claim 16, wherein a valve is disposed between the biosensor and the collecting chamber creating a discontinuity between the extracted interstitial fluid and the interstitial fluid being analyzed by the biosensor.

27. The device of claim 12, wherein said pump is a peristaltic pump, a diaphragm pump, or a piston pump.

28. The device of claim 12, wherein said negative pressure generated by the pump is from about 2 kPa to about 98 kPa.

29. The device of claim 12, wherein said vacuum generated by the pump is pulsed or continuous.

30. The device of claim 16, wherein said biosensor comprises a Bis(2,2-bipyridyl)dichloro Osmium(II), complexed with poly(1-vinylimidazole) mediator in conjunction with a dispersed electronic conductor.

31. The device of claim 12, wherein said device further comprises a sampling chamber connected to the extraction chamber by a pumping conduit, said sampling chamber collects the extracted interstitial fluid from the skin for its analysis.

32. The device of claim 31, said sampling chamber is continuously sealed by a septum connected to the sampling chamber.

33. The device of claim 24, said device further comprising a microcontroller connected to the pressure sensor in order to monitor and control the pressure above the skin and inside the extraction chamber.

34. A method for electro-suturing the skin from a subject comprising the steps of:
electroporating the skin by applying a non-pulsed floor voltage 4 volt to 8 volt at a current intensity between 0.1 mA to 0.25 mA before and during an applied pulsed voltage comprised between 20 volt to 90 volt at a current intensity between 0.1 mA to 0.25 mA between two electrodes;
applying a negative pressure at or near the region of the skin being electroporated, the simultaneous combination of electroporating the skin and applying the negative pressure forming openings in the skin for suturing the skin and for extracting the interstitial fluid, the interstitial fluid being extractable only so long as the negative pressure is applied in combination with electroporating the skin; and
collecting the extracted interstitial fluid from the skin.

35. The method of claim 34, further comprising the step of analyzing the concentration of an analyte or a plurality of analytes in the interstitial fluid extracted from the skin.

36. The method of claim 34, wherein a non-pulsed voltage and a pulsed voltage are generated between at least a first moving or stationary electrode and a second stationary electrode for electroporating the skin.

37. The method of claim 35, wherein the analyte is glucose.

38. The method of claim 34, wherein said negative pressure is about 2 kPa to about 98 kPa.

39. The method of claim 35, further comprising the step of transmitting the analysis of the concentration of the analyte in the extracted interstitial fluid from the skin.

40. The method of claim 35, wherein the collecting of the interstitial fluid and the analyzing of the concentration of the analyte in the extracted interstitial fluid are regulated by a check valve.

41. The method of claim 34, wherein the negative pressure is pulsed or continuous.

42. The method of claim 34, wherein the negative pressure applied at or near the region of the skin is monitored by a pressure sensor.

43. The method of claim 34, wherein the subject is an animal or a human.

44. The method of claim 40, wherein the check valve is a one-way valve.

* * * * *